US005722464A

United States Patent [19]
Truyen et al.

[11] Patent Number: 5,722,464
[45] Date of Patent: Mar. 3, 1998

[54] PILE WARP THREAD TENSION CONTROL APPARATUS FOR TERRY CLOTH WEAVING

[75] Inventors: Walther Truyen, Oudenaarde; Adnan Wahhoud, Lindau-Bodolz; Peter Czura, Wangen; Hans-Dieter Scorl, Lindau; Josef Hehle, Hoerbranz; Werner Birner, Lindau-Bodolz, all of Germany

[73] Assignee: Lindauer Dornier Gesellschaft mbH, Lindau, Germany

[21] Appl. No.: 689,709

[22] Filed: Aug. 16, 1996

[30] Foreign Application Priority Data

Aug. 17, 1995 [DE] Germany .............. 195 30 333.2

[51] Int. Cl.⁶ .................................................. D03D 39/22
[52] U.S. Cl. .................................................. 139/25
[58] Field of Search .................................. 139/25, 26

[56] References Cited

U.S. PATENT DOCUMENTS

| | | | |
|---|---|---|---|
| 4,112,981 | 9/1978 | Freisler | 139/25 |
| 4,974,639 | 12/1990 | Maitan et al. | 139/25 |
| 5,392,817 | 2/1995 | Seifert et al. | 139/25 |
| 5,441,084 | 8/1995 | Corain et al. | 139/25 |
| 5,458,160 | 10/1995 | Geiger et al. | |

FOREIGN PATENT DOCUMENTS

| | | |
|---|---|---|
| 0271021 | 6/1988 | European Pat. Off. |
| 0352791 | 1/1990 | European Pat. Off. |
| 0443343 | 8/1991 | European Pat. Off. |
| 4432452 | 3/1995 | Germany |

*Primary Examiner*—Andy Falik
*Attorney, Agent, or Firm*—W. G. Fasse; W. F. Fasse

[57] ABSTRACT

The weaving of terry cloth is improved by preventing slackening of the warp threads during beat-up. The warp threads are kept in contact with a warp tensioning faller roller (8) at all times. For this purpose the faller roller (8) is eccentrically mounted and biased by a spring (46) retraction force applied through a control lever (48). The force of the spring (46) is in balance with the tension on the warp threads (4), whereby the spring (46) causes a warp length compensation during shed formation. A piston rod (52A) of a piston cylinder drive (52) acts on the control lever (48) of the faller roller (8). By pressurizing the cylinder (52), the faller roller (8) is tilted about an eccentrically mounted bearing shaft (14) and a rated pile warp thread length (54) is delivered or fed, without the pile warp threads (4) lifting away from the faller roller (8). One chamber of the drive cylinder (52) is periodically pressurized in synchronism with the terry cloth drive (17) for the beat-up of a group of weft yarn threads or both chambers of the drive cylinder (52) are pressurized for weaving a border or trim.

18 Claims, 6 Drawing Sheets

PILE WARP THREAD TENSION CONTROL APPARATUS FOR TERRY CLOTH WEAVING

FIELD OF THE INVENTION

The invention relates to an apparatus for controlling the warp tension in pile warp threads and for providing controlled supply rates of pile warp yarn sufficient for forming loops in the manufacture of terry cloth on weaving looms.

BACKGROUND INFORMATION

U.S. Pat. No. 5,458,160 (Geiger et al. describes a control system for controlling the tension on a pile warp yarn (4) and for providing a controlled pile warp yarn delivery or supply rate (54) in the manufacture of terry cloth on weaving looms with a warp let-off controlled pile warp beam (2), from which the pile warp thread (4) is let off over at least one guide roller (5) and over a dancing or floating roller (8) while a pile warp tension is continuously maintained, and wherein a pile warp yarn delivery length (54) is supplied in accordance with the delivery or supply rate prior to each beat-up of a group of weft yarns by a reed (22) and prior to a controlled displacement of the fabric (18) beat-up edge (19) that takes place in the direction of the beat-up direction of the reed (22).

The foregoing U. S. Patent corresponds to German Patent DE 4,310,840 C1. In this reference a tensioning roller, also referred to as a floating roller or faller roller, and its control play a central role in controlling the tension of the pile warp threads. In the manufacture of terry cloth, the tensioning roller assembly has several tasks, namely:

a) providing a length of pile warp thread with the required delivery rate controlled by the fabric control;

b) ensuring a yarn length compensation when forming the shed;

c) assuring the delivery of a pile warp yarn length or rate sufficient for the forming of a row of loops with each beat-up of a group of weft threads by the reed; and finally d) the momentary position of the tensioning or faller roller serves for ascertaining the tension on the pile warp threads by a pile warp tension sensor whereby the faller roller is arranged to swing or oscillate relative to the position of a stationary guide roller positioned in the path of the pile warp threads between the pile warp beam and the faller roller.

Technical limits have been encountered regarding a further increase in the productivity of the weaving machine by increasing the r.p.m. of the loom. These limits are due to limitations imposed by the dynamic operation sequence of the faller roller assembly. Questions relating to the dimensioning, arrangement, and the interaction of the elements that control the operational sequence on the pile warp threads downstream of the pile warp beam play a decisive role in the loom r.p.m. Particularly, the construction of the guide roller, the arrangement of the faller or tensioning roller and the control that synchronizes the tensioning roller motion with the warp let-off mechanism and with the terry apparatus, have a significant influence on the loom r.p.m.

The speed limits of the dynamic operational sequence become apparent from, among other factors, the slackening of the tension of the pile warp threads which are guided around the faller roller, to such an extent during the beat-up of a group of weft threads that the pile warp threads lift away from the surface of the faller roller. Due to this lifting away of the warp threads from the faller roller and due to the existing twist of the warp threads, the warp threads get tangled with each other. The tangled warp threads then twist into cords, which disrupts the formation of the pile and can lead to warp thread breakage. Furthermore, the pile warp thread mass between the pile warp beam and the beat-up edge of the fabric is caused to oscillate by the warp let-off action of the warp let-off mechanism. Such oscillation also has an unfavorable effect on the proper guidance and tensioning of the pile warp threads.

OBJECTS OF THE INVENTION

In view of the above it is the aim of the invention to achieve the following objects singly or in combination:

to provide a control system for influencing or controlling the tension of the pile warp threads and for providing a supply rate for the pile warp delivery length in the manufacture of terry cloth, to increase the productivity of a weaving loom by separating the integral or inherent functions of the faller roller and allocating these functions to separate devices;

to prevent, as much as possible, the pile warp mass from vibrating or oscillating between a guide roller and the tensioning or faller roller when letting off warp yarn and articularly also when a group of weft threads is being beat up;

to maintain a constant tension of the warp threads between the glide roller and the faller roller on the one hand and between the guide roller and the pile warp beam on the other hand, to prevent the pile warp threads from getting tangled on their way from the warp beam to the beat-up line;

to assure dynamically that the applied warp tension is always equal to the instantaneously required or rated warp tension;

to compensate for warp thread length changes that occur during beat-up;

to maintain and control the required warp thread delivery rate at the required warp tension along the entire warp thread length between take-off and beat-up at all times during weaving; and to control the warp thread for achieving a required pile height in a terry cloth.

SUMMARY OF THE INVENTION

The above objects have been achieved by the invention in a control system that combines the following features. A warp guide roller (5) is preferably provided with a friction enhancing roller surface for applying a frictional force to a warp thread (4) looping, at least partly, around the guide roller (5) which is driven by its own motor. A warp tension or faller roller (8) is eccentrically and rigidly mounted to a shaft (14) which is rotatably mounted at its ends in respective movable support brackets (9) which in turn are rotatably mounted on a respective journal (11, 12) fixed to a loom frame member (10). The rotational axis (14A) of the shaft (14) is spaced radially from the rotational axis (12A) of the respective stud (12). At least one end of the warp tensioning roller (8) is rigidly connected to at least one control lever (48) biased by a spring (46). Specifically, one end of the spring (46) is connected to a connector element (50) of the control lever (48) while the other spring end is connected to a tension or pull bolt (59) which is secured in a position adjustable manner to the respective support bracket (9). A coupling member (16) operatively connects the respective support bracket (9) to a terry cloth drive (17) for adjusting the position of the respective bracket in synchronism with the terry drive (17). A controllable drive mechanism (52) mounted to the loom frame (10) is operatively connected, for example by a rod (52A), to the spring biased control lever (48) for oscillating the control lever and thus the faller or tensioning roller.

The movable support brackets (9) are preferably rotatably arranged in a bearing position on the rear side wall sections of the weaving loom frame (10) in which the tensioning roller (8) biased by a tension force (46) is supported at (13, 14) at a vertical distance from the rotational axis (11) of the support bracket (9). At least one of the support brackets is functionally connected to at least one conventional terry cloth drive (17) for displaying or moving the fabric, whereby synchronism is enforced between the motion of the terry cloth drive and the motion of the tensioning or faller roller (8).

According to the invention the warp tensioning or faller roller (8) is mounted eccentrically in the support brackets (9), whereby the position of this roller (8) can be varied relative to the rotational axis of the support brackets. Such a positional change of the faller roller (8) ensures that by applying a force to a position control lever (48) rigidly connected to the roller (8), the roller (8) is caused to swing out so that a specific or rated length (54) of the pile warp that loops at least partly around the roller (8), i.e. a so-called delivery rate length of the pile warp thread, is released in the direction of the fabric formation, without thereby relieving the tension on the pile warp thread so much that the pile warp thread would lift away from the surface of the tensioning roller (8) around which the warp thread is looped.

A further preferred feature of the invention is seen in that the ends of the tensioning roller are operatively connected to a spring tensioning mechanism that adjusts the warp tension so that a tension force is exerted on the tensioning roller and thus on the pile warp thread, which tensioning force is balanced with the required primary tension on the pile warp threads.

The spring tensioning mechanism (46, 51, 61) effective on the tensioning roller assures a compensation of the length of the pile warp thread during shed formation because the spring tensioning mechanism is effective independently of the terry cloth drive, contrary to the operation of the support brackets (9) which is synchronized with the terry drive (17).

Furthermore, according to the invention it is preferred that the controllable drive effective on each spring tensioning mechanism is a pneumatically operated piston cylinder unit (52) that is capable of swinging the tensioning roller about its eccentrically arranged axis at a certain point of time within the weaving process, namely shortly before or prior to the beat-up of a group of weft threads, so that the pile warp threads are supplied with a predetermined pile warp yarn delivery length or rate during the beat-up operation while the tension on the pile warp is maintained. The tensioning or faller roller does not lift away from the pile warp threads in the direction toward the cloth or beat-up line when the spring retraction is partially relieved, but simply swings about its rotational axis. This results in the desired advantageous effect that the necessary pile warp delivery length is supplied at the required rate, while simultaneously a necessary measure of tension on the pile warp threads is maintained.

The spring tensioning mechanism of the invention comprises at least one control lever rigidly connected to the tensioning roller. The free end of the control lever is coupled through at least one tension spring (46) to a coupling point while the other end of the spring acts on a tie (59) or tension bolt that is adjustably connected with the tiltable support bracket. Furthermore, the tie bolt is connected to a threaded spindle (58) that bears against the support bracket (9) and serves for adjusting the biasing force of the tension spring (46). For example by the threaded spindle is connected to a corresponding drive, such as a motor drive (61).

A pile warp tension measuring device or sensor (56) is preferably arranged in the area of the pile warp threads between the tensioning roller and the guide roller for detecting the actual warp tension between the guide roller and the tensioning roller The actual value of the warp tension is preferably readable from a corresponding optical display and, if necessary, the tension can be adjusted manually by rotating the threaded spindle, e.g. with a crank. Alternatively or additionally, if a motor driven control is used, a control signal is provided by comparing the actual biasing force with the rated or required biasing force. The respective control signal is fed as an analog signal to a motor (61) connected with the threaded spindle for regulating or controlling the tension force on the warp threads.

Finally, according to the invention it is preferable that the guide roller (5) is connected to a controlled motor drive so that the pile warp threads that are continuously supplied by the warp let-off beam (2) are fed to the weaving process while a constant pile warp tension is simultaneously maintained between the guide roller and the tensioning roller. It is important that the guide roller drive can also be controlled as a function of the tension values determined by the tension measuring device or sensor. This feature has the advantage that the motor-controlled guide roller can influence or control the warp tension, both on the warp strand or thread section between the warp beam and the guide roller and on the warp strand or thread section between the guide roller and the tensioning roller. Such a control of the warp tension suppresses the vibrations of the pile warp threads in the mentioned warp thread sections.

BRIEF DESCRIPTION OF THE DRAWINGS

In order that the invention may be clearly understood, it will now be described, by way of example, with reference to the accompanying drawings, wherein.

DETAILED DESCRIPTION OF PREFERRED EXAMPLE EMBODIMENTS AND OF THE BEST MODE OF THE INVENTION

Figure 1:
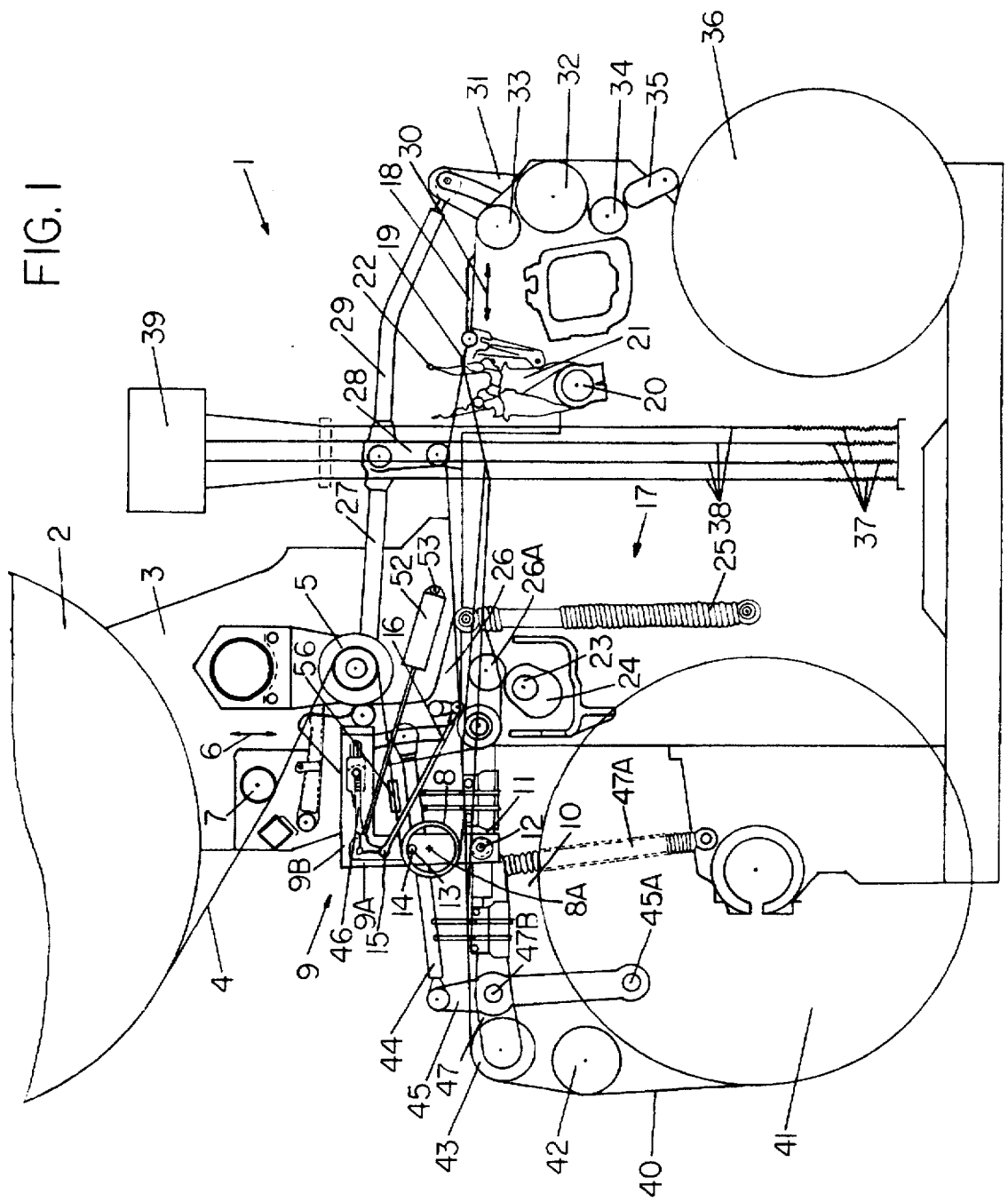
FIG. 1 is a schematic illustration of a side view of a weaving loom with a control system for controlling the warp tension according to the invention.

FIG. 1 shows a pile warp beam 2 in its raised position on a weaving loom 1. The pile warp beam 2 is rotatably supported by a shaft or axis (not shown) which is supported in a loom frame member 3. A pile warp thread 4 is guided by conventional elements, including a known warp let-off apparatus (not shown), from the pile warp beam 2 under a tensioning roller 7 which is variable in its position in the direction indicated by a double-headed arrow 6. The tensioning roller 7 is also mounted on the loom frame element 3. The warp thread 4 passes from the tensioning roller 7 to a guide roller 5 driven by a motor 5A, such as a d.c. motor integrated into the roller 5. The pile warp thread 4 is then guided around a faller roller or further tensioning roller 8. Preferably, the guide roller 5 has a friction enhancing surface 5' to exert a friction force on the pile warp thread 4. Such a friction surface 5' may, for example be realized by a rubber jacket or coating on the surface of the roller 5.

According to the invention, the faller roller 8 is rotatably supported at each end in a respective bracket 9. These support brackets 9 are journalled to the rear loom frame side walls 10 by a bearing journal or stud 12 in a bearing 11, see FIG. 3. Each support bracket 9, one at each roller end, is constructed as an angle lever that has a vertical leg 9A and a horizontal leg 9B. The bearing journal or stud 12 is rigidly fixed to the free end of the vertical leg 9A of the support bracket 9. The vertical leg 9A of each support bracket 9 has a bearing 13 that is positioned at a spacing from the center axis 12A of the bearing journal 12 (see FIG. 3). A bearing shaft 14 having a center axis 14A is rigidly connected to the faller roller 8. The bearing shaft 14 is arranged eccentrically to the center axis 8A of the faller roller 8. Further, the shaft 14 is rotatably supported with its ends in the bearings 13. In a preferred embodiment, one end 16A of a connecting rod or coupler 16 is coupled to the support bracket 9 at a journal 15 that is arranged above the bearing 13 and that includes, for example, an oblong hole or slot 9C for adjusting the position of the journal 15 along the slot 9C, see also FIG. 3, while the other end 16B of the coupling rod 16 is pivoted or journalled to a conventional terry cloth drive 17. Identical components provided at each side of the loom are described only once.

The terry drive 17 controls an oscillating displacement of a fabric 18 relative to a fixed beat-up point or line 19 against which the group of weft threads, not shown, is beat up by a reed 22 shown in FIG. 1 that is connected to a weaving sley 21 which is mounted to tilt about its rotational axis 20.

Figure 3:
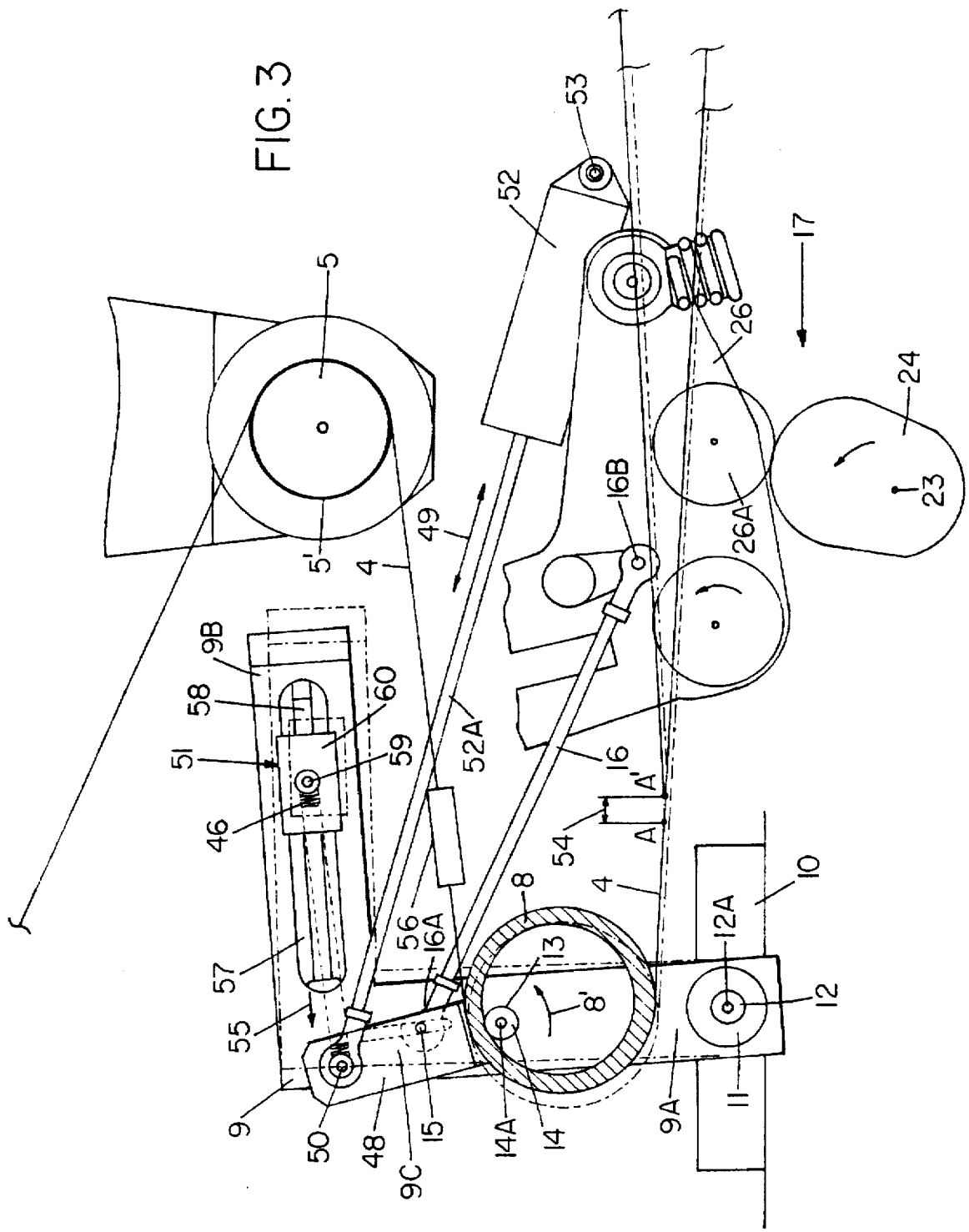
FIG. 3 shows, on an enlarged scale, a portion of the side view according to FIG. 1 showing the tensioning roller at the time of supplying or feeding a rated pile warp thread length.

Referring to FIGS. 1 and 3, the conventional terry cloth drive 17 comprises a terry cloth beam 23 and at least one eccentric cam 24 arranged on the beam for rotation with the beam 23. A cam follower roller 26A supported on a control arm or lever 26 maintains contact with the curved surface of the cam 24. One end of a first connecting rod or coupler 27 is pivoted to the control arm or lever 26. The other end of the rod 27 is connected by a connecting piece 28 to a second connecting rod or coupler 29 linked by a connection (not shown) to a lever arm 31 connected to a feed roller 32 that moves the fabric 18 in the direction of a double arrow 30 in a back and forth oscillating manner.

A basic or main warp beam 41 for supplying the main warp 40 is rotatably supported in the rear frame side wall 10 of the weaving loom 1. The main warp 40 is guided form the main warp beam 41 over a guide roller 42 and a back rail or yarn rest 43 to the shed forming devices that are illustrated here schematically, by way of example, by a jacquard device 39 with harness ties 38 and retracting or pull-back springs 37. The back rail or yarn rest 43 is supported at one end of a double arm 47 biased by a spring 47A for executing a so-called basic terry cloth motion upstream of the terry cloth drive 17 as viewed in the feed advance direction from left to right in FIG. 1. The double arm 47 is mounted in a journal 47B arranged in a single-arm lever 45 that can rotate about an axis 45A rigidly held in the weaving loom frame. A connecting rod 44 is connected to the free end of the lever 45. The rod 44 is further functionally connected to the control arm 26 of the terry cloth drive 17.

Figure 2:
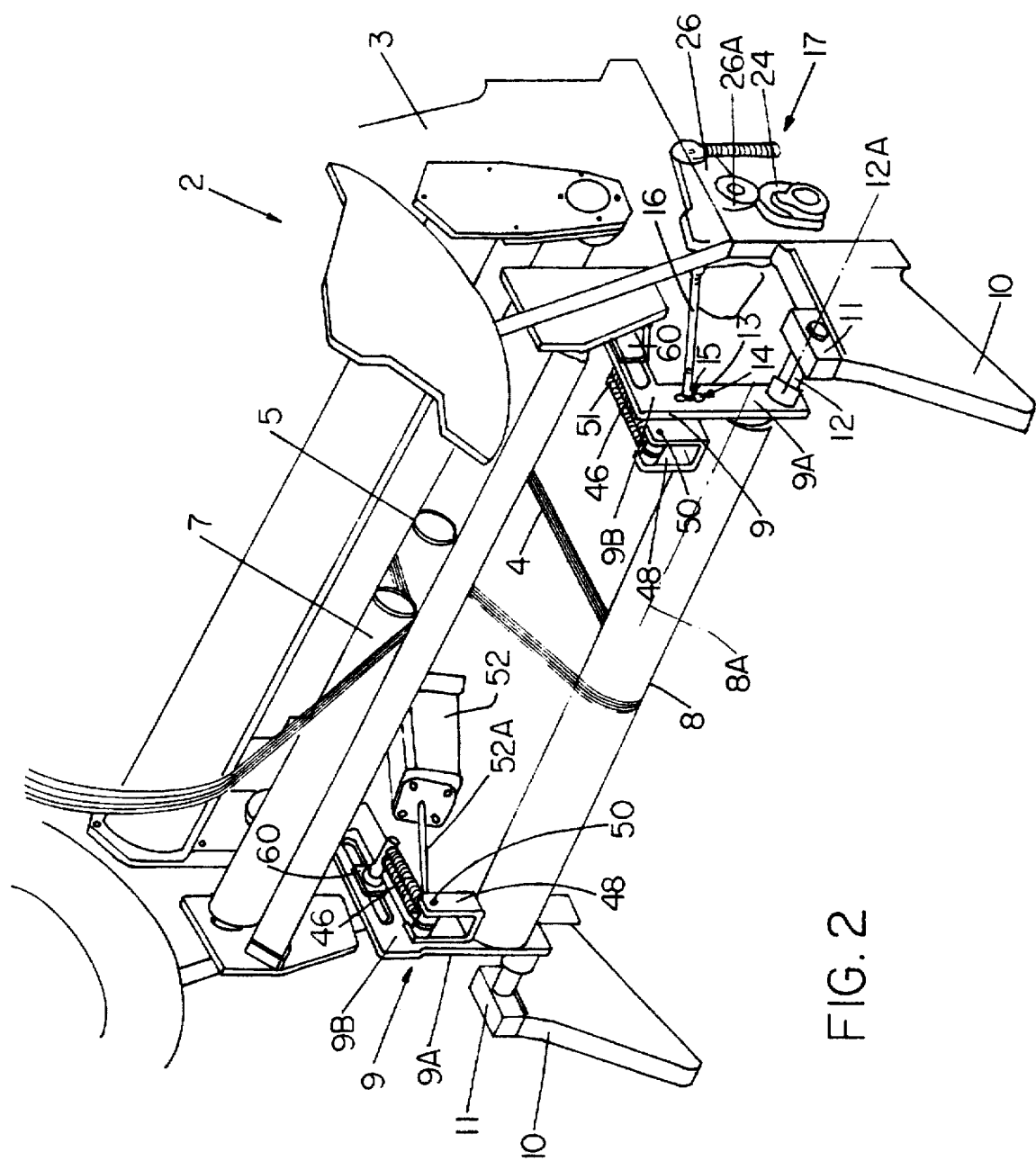
FIG. 2 is a perspective view of the part of the weaving loom showing the present control system as seen from the warp beam side.

Further characteristic features according to the invention are shown in FIG. 2. One support bracket 9 including its horizontal leg 9B and its vertical leg 9A, is rotatably mounted by the bearing journal or stud 12 in the respective bearing 11 in each loom side wall 10, respectively. A connecting rod or coupler 16 is journalled in a bearing 15 of the vertical leg 9A to connect the support bracket 9 with the terry cloth drive 17. Thus, the cam follower roller 26A is connected to the control arm 26 for transmitting the terry motion from the cam 24 to the support bracket 9 in synchronism with the motion of the rotating drive unit for the cam 24. The bearing 13 is arranged in the support bracket 9 at a vertical spacing from the central axis 12A of the bearing journal or stud 12. The bearing shaft 14 is rigidly and eccentrically attached to the faller roller 8 relative to the center axis 8A of the roller 8. The shaft 14 is rotatably mounted in the bearing 13 for rotation about a center axis 14A. The shaft 14 is long enough to extend through both ends of the faller roller 8 that is preferably constructed as a hollow tube to reduce weight. However, the bearing shaft 14 could be replaced by two journal studs eccentrically secured to the ends of the faller roller 8. A control lever 48, preferably having a U-cross-section, is rigidly secured to the outer circumference at least at one free end area of the roller 8. One end of at least one tension spring or a tension spring assembly 46 acts through a connecting element 50 such as a journal pin on the control lever 48, see FIGS. 2 and 3. The other end of the spring 46 is pivoted to a spring tension device 51 that is arranged on the horizontal leg 9B of the support bracket 9. The spring tension device 51 is secured to the horizontal leg 9B of the support bracket 9 in an adjustable manner. Thus, it is achieved that the faller roller 8 that applies tension to the pile warp threads 4, assures a pile warp thread delivery at the required length rate 54 just before the reed beats up a group of weft threads while simultaneously maintaining proper tension on the pile warp threads 4. This tension is maintained, even through the coupler 16 operated by the terry drive 17 moves the support bracket 9 in a tension release direction. Such release of the pile warp threads 4 is compensated by the control of the position of the roller 8 according to the invention.

FIG. 3 shows with a full line the displaced position of the faller roller 8 and the displaced position of the support bracket 9 during the beat-up of a group of weft threads by the reed 22 shown in FIG. 1. The normal position is shown by dash-dotted lines. The terry cloth drive 17 tilts the support bracket 9 through the coupler 16 about the bearing journal or stud 12 in the bearing 11, in the direction of the arrow 55 counterclockwise. At the same time, a drive unit 52 is activated to push the control lever 48 in the direction of an arrow 49 through the piston rod 52A connected by a connecting journal pin 50 to the lever 48 that is rigidly connected to the faller roller 8 to tilt the roller 8 counterclockwise as shown by the arrow 8'. The drive unit 52 may, for example, be a double-acting pneumatically operated piston-cylinder device that is pivoted to the weaving loom frame at a fixed loom frame point 53. As a result, the faller roller 8 that is rigidly fixed to the bearing shaft 14, tilts about the center axis 14A of the shaft 14 thereby releasing a rated length 54 of pile warp thread as measured between two points A and A' in the fabric forming direction. Due to the eccentric mounting of the faller roller 8 and due to the merely partial release of the spring tension on the faller roller 8 by the piston-cylinder unit 52, the pile warp thread 4 does not lift away from the circumference of the faller roller 8.

As shown in FIGS. 1 and 3 a pile warp thread tension sensor device 56 is integrated or mounted to the loom frame in the pile warp thread area between the guide roller 5 and the faller roller 8. The tension sensor 56 is constructed, for example, as an absolute sensor connected to transmit signals to an electronic central or main loom control MLC shown in FIGS. 4, 5, and 6. The MLC as such is of conventional construction.

Figure 4:
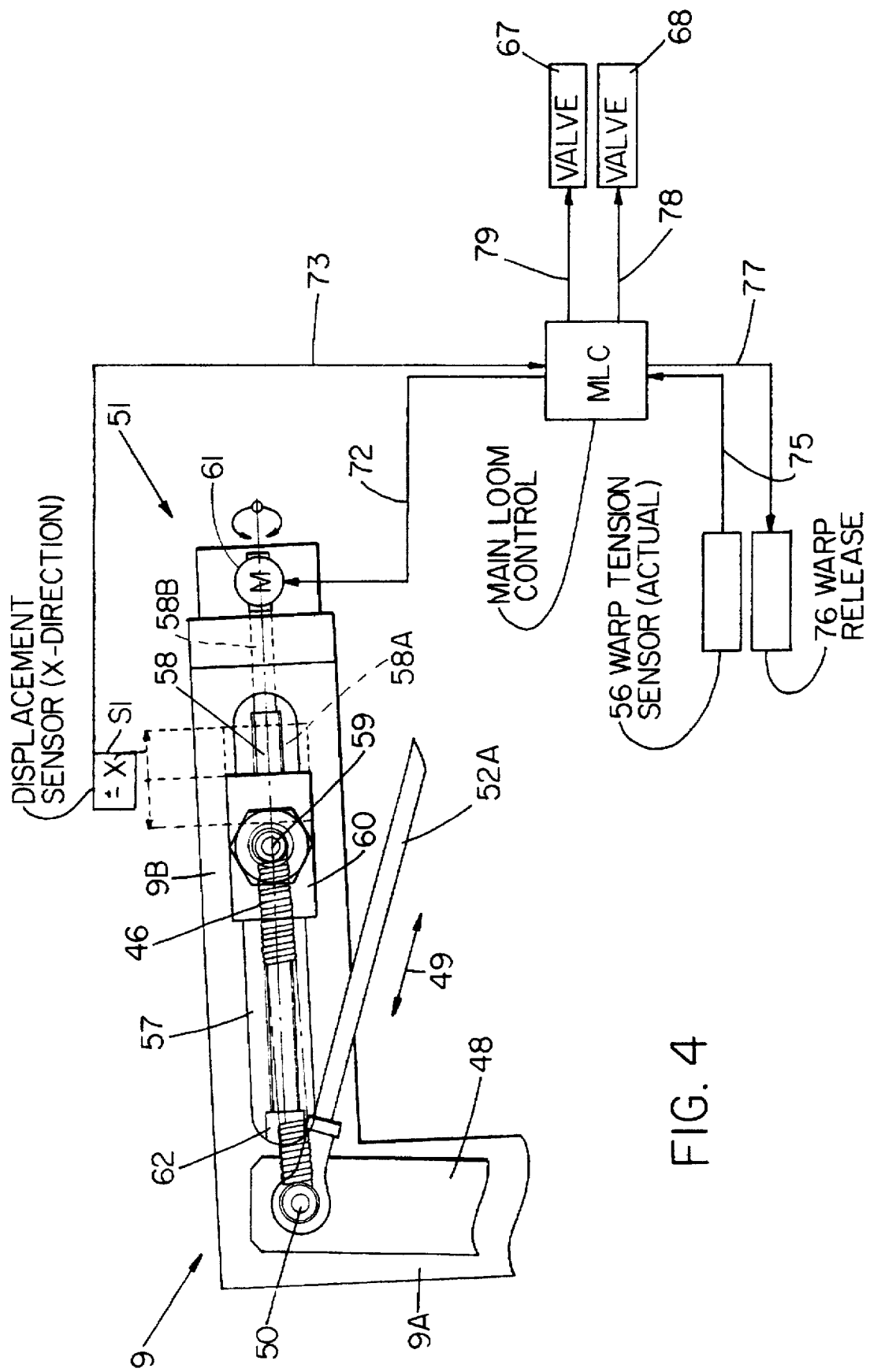
FIG. 4 shows a spring tensioning mechanism with a motorized drive for adjusting the retracting force of a warp tensioning spring to a predetermined value.

The pile warp thread let-off control is influenced by comparing actual and rated values for the warp tension in the main loom control MLC to provide a pile warp tension signal which is used to keep the warp thread tension at the rated value. Furthermore, the tension force of the spring 46 can be controlled by a spring tensioning device 51 if the actual value of the tension force deviates from the rated value as determined by the above comparing in the main loom control MLC. For this purpose a guide slot 57 is arranged in each upper leg 9B of the support bracket 9. A slider or slide member 60 runs along each of the guide slots 57 and a tie bolt 59 passing through the slider 10 is guided in the respective guide slot 57. Each slider 60 is connected to a respective threaded spindle 58. The slider 60 for the tie bolt 59 has a lateral guide surface that contacts the outer side surface of the leg 9B of the support bracket 9. The right or free end of the threaded spindle 58 is, for example, equipped with an actuating drive 61 such as an electric motor, as shown in FIG. 4. Additionally, the right end of the spindle 58 is rotatably held in bearing 58B in the leg 9B of the bracket 9.

FIG. 4 shows the spring tensioning device 51 for the spring 46. One device 51 is connected to each support element 9 for tensioning or adjusting the biasing force of the respective spring 46. The above mentioned threaded spindle 58 is mounted with its left end to bear for example against a partly shown abutment bearing 62 that is rigidly connected to the support bracket 9, but the left spindle end can rotate in the abutment bearing 62. The threaded spindle 58 is threaded female for example into an internal threading 58A of a threaded element which is preferably an integral part of the slider 60. The tie bolt 59 connects the right end of the spring 46 to the slider 60. In the preferred embodiment, the free end of the threaded spindle 58 is connected to the above mentioned actuating drive 61 embodied by a controllable electric motor. The spring 46 is pivoted with its left end to the connecting journal pin 50 of the control lever 48. Thus, the spring is held between the pin 50 and the tie bolt 59 and its tension force is adjustable by the motor drive 61 for adjusting the position of the slider 60 along the slot 57 by rotating the threaded spindle 58 that engages the internal threading 58A in the slider 60. Thus, the tension force applied to the faller roller 8 is correspondingly controlled through the lever 48, whereby the pile warp thread that loops around the faller roller 8 is kept at the proper tension at all times. A manual rotation of the spindle 58 by a crank not shown is additionally possible.

Referring further to FIG. 4, a first sensor S1 measures the displacement±X (in the X-direction) of the guide slider 60 in response to the rotation of the spindle 58 by the motor 61. This actual displacement signal is supplied through an electrical conductor 73 to the main loom control MLC having a memory wherein a rated displacement is stored for comparing with the actual displacement to provide a control signal for the motor 61. This control signal is fed to the motor 61 through a signal conductor 72 from the MLC for controlling the proper warp tensioning in closed loop feedback fashion while weaving terry cloth.

FIG. 4 also shows that the actual warp tension as represented by a signal produced by the warp tension sensor 56, is processed in the MLC connected to the sensor 56 through a signal conductor 75. The MLC produces a warp release signal in response to the signal from the warp tension sensor 56 and feeds the warp release signal on a control conductor 77 to the warp release 76 in a closed loop feedback control manner.

FIG. 4 further shows that two flow control valves 67 and 68 are connected through respective control conductors 79, 78 to the MLC. These valves operate the above mentioned piston cylinder drive unit 52 as will be described in more detail below with reference to FIG. 5.

Figure 5:
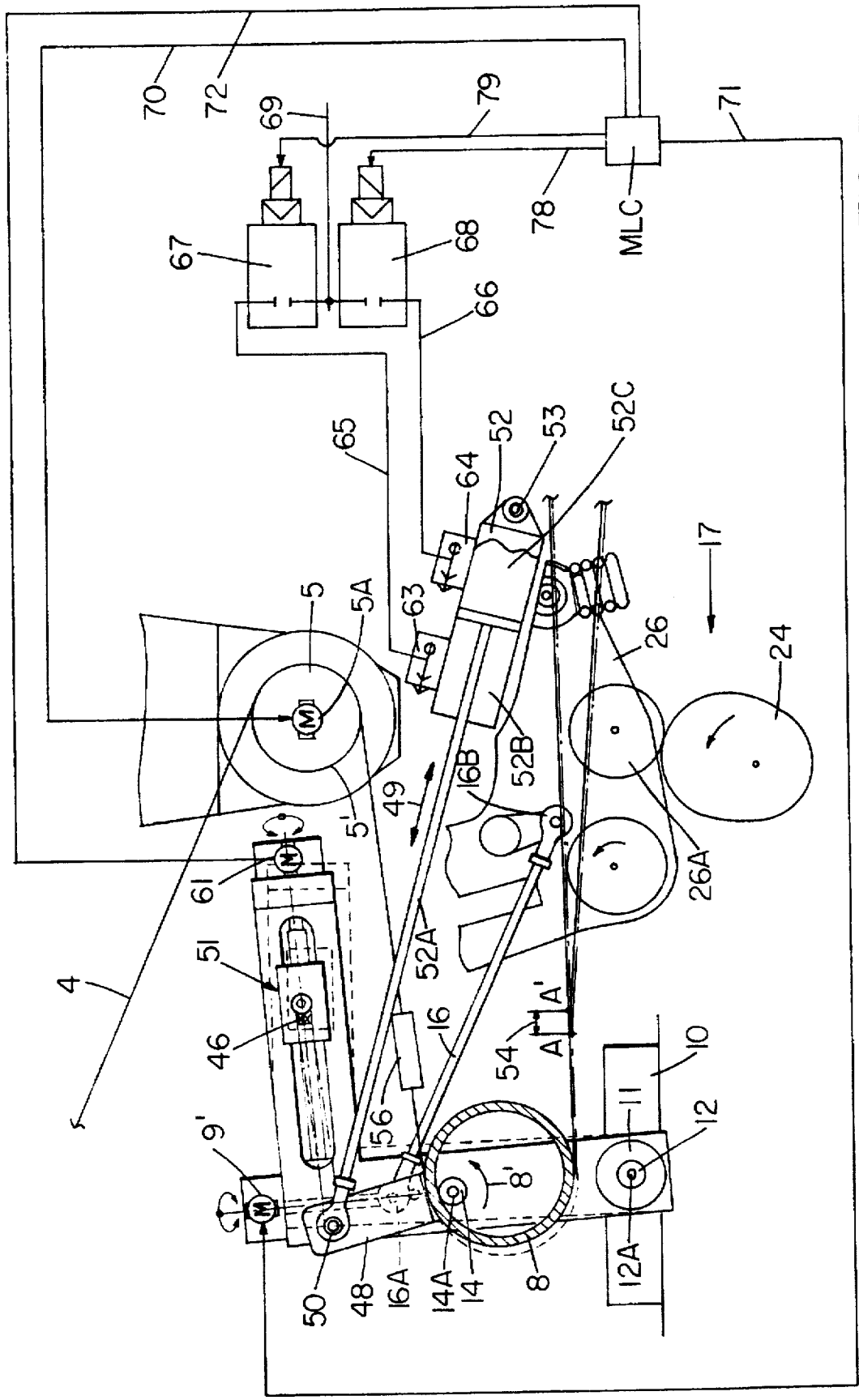
FIG. 5 shows a pneumatically controlled drive unit for dynamically adjusting the position of a warp tensioning roller to determine a pile warp thread delivery rate in an X-direction corresponding to a fabric take-up direction.

FIG. 5 shows the influence of the drive unit 52 on the faller roller 8 for delivering or feeding a rated pile warp thread length 54 at the required rate before the beat-up of a group of weft threads by the reed 22 shown in FIG. 1. The drive unit 52 is constructed, for example, as a double working pneumatically operated piston-cylinder unit. The cylinder volume 52B on the side toward the piston rod 52A and the cylinder volume 52C on the side facing the backside of the piston are each connected to a controlled quick venting valve 63, 64, respectively. A working or output line 65, 66 is connected to each valve 63, 64, respectively, and leads through line 69 and controllable valves 67, 68 to a pneumatic pressure source (not shown). By pressurizing the volume 52C through valve 64 the piston tilts the control lever 48 connected to the piston rod 52A together with the faller roller 8 counterclockwise (arrow 8'), whereby the tensioning force of the spring 46 is partially counteracted and a rated length 54 of pile warp threads is fed for forming a row of loops in the course of beating-up a group of weft threads. Similarly, pressurizing the cylinder volume 52B through valve 63 moves the piston rod in the opposite direction bringing the faller roller 8 into the dashed line position shown in FIG. 5 to increase the warp tension. Arrow 49 indicates the back and forth movement of the piston rod 52A in response to the operation of the control valves 67, 68 which receive their respective control signals through the conductors 79, 78 from MLC. A valve control program is stored in the memory of the MLC for the operation of the drive 52 in synchronism with all other loom operations.

FIG. 5 also shows the control conductors 70, 71, and 72 connecting the drive motors 5A, 61, and 9' to the MLC. The roller drive motor 5A is driven in synchronism with the loom operation through conductor 70. The motor 61 is also driven in synchronism with the loom operation through conductor 72.

Figure 6:
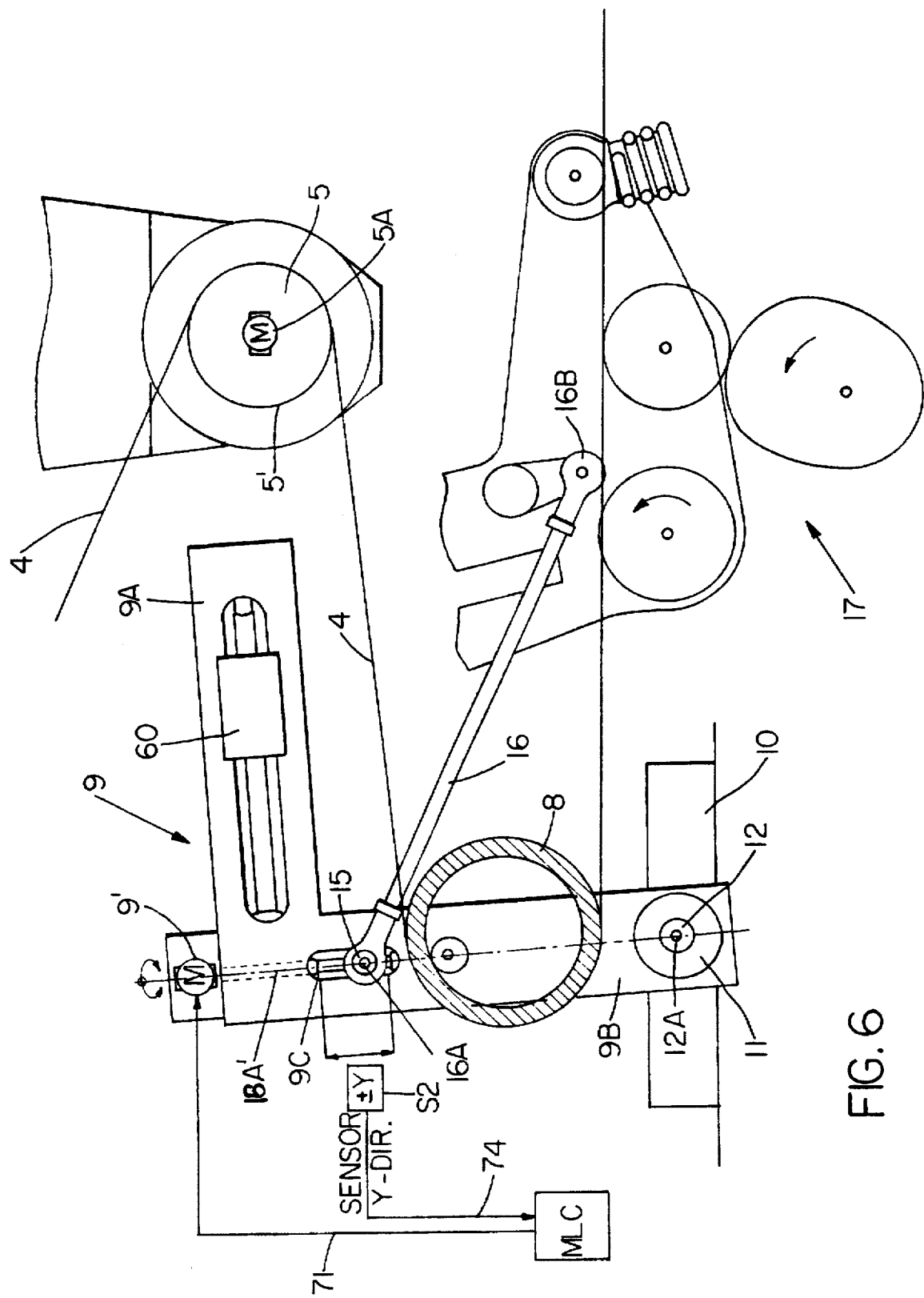
FIG. 6 illustrates an adjustment mechanism for adjusting a pile height in the y-direction.

Referring to FIG. 6, the motor 9' receives its closed loop control signal through the conductor 71 from the MLC for adjusting the position of the journal 15 along the length of the slot 9C in the leg 9B of the support bracket 9. The upper end 16A of the coupler rod 16 is operatively secured to the journal 15. The lower end 16B of the rod 16 is pivoted to the terry cloth drive 17, whereby the oscillating tilting motion of the support bracket 9 about its journal axis 12A is synchronized with the operation of the terry cloth drive 17 through the coupler rod 16.

By displacing the journal 15 along the slot 9C the effect of the terry drive 17 on the back and forth tilting of the support bracket 9 is variable. More specifically, the height of the warp pile is adjustable by displacing the journal 15 along slot 9C. A second sensor S2 measures the substantially vertical actual displacement±Y (in the Y-direction) and feeds a respective signal through the conductor 74 to the MLC which produces a respective control signal supplied through the conductor 71 to the motor 9'. The control signal on the conductor 71 is, for example, produced by comparing the actual displacement signal Y with a rated Y-displacement signal stored in the memory of the MLC to provide a respective closed loop feedback signal.

The motor 9' drives a spindle 16A' which engages a threading in the end 16A of the rod 16, thereby moving the end 16A, and with it the journal 15, up or down depending on the drive direction of the shaft of the motor 9'. This drive is quite similar to the above described back and forth drive with the motor 61 and spindle 58.

As is known, no group of weft yarns is formed for the border or trim weave. Therefore, no pile warp threads delivery length 54 must be supplied in the border area. For the purpose of forming the trim or border, the cylinder space 52B is continuously pressurized during the time of border weaving or the motion of the piston rod 52A is at least blocked.

Although the invention has been described with reference to specific example embodiments, it will be appreciated that it is intended to cover all modifications and equivalents within the scope of the appended claims.

What is claimed is:

1. An apparatus for controlling the pile warp thread tension for weaving terry cloth in a loom, comprising a loom frame, at least one guide roller (5) rotatably mounted in said loom frame, a drive motor (5A) connected to said at least one guide roller (5), a warp tensioning faller roller (8) having a central axis (8A) and two ends, two support brackets (9) one of which is mounted to said loom frame (10) at each end of said faller roller (8), first bearings (11, 12) fixed in said loom frame (10) and rotatably mounting said support brackets (9) to said loom frame, second bearings (13, 14) rigidly connected to said faller roller (8) eccentrically to said central axis (8A) of said faller roller (8), said second bearings (13, 14) rotatably mounting said faller roller (8) to said support brackets (9), said first bearings (11, 12) and said second bearings (13, 14) being spaced from each other, at least one spring biased control lever (48) rigidly connected to said faller roller (8) for tilting said faller roller (8), at least one biasing spring (46) operatively connected with one spring end (50) to said control lever (48) and with another spring end (59) to said support bracket (9), a coupling link (16) connected with a first link end (16A) to said support bracket (9) and with a second link end (16B) to a terry drive (17), and a controllable drive (52) operatively connected to said loom frame (at 53) and to said spring biased control lever (48) for oscillating said faller roller (8) through said control lever (48) to maintain a substantially fixed warp tension simultaneously with a required warp supply rate.

2. The apparatus of claim 1, wherein said guide roller (5) has a friction surface for applying a friction force on the warp thread (4).

3. The apparatus of claim 1, wherein said first bearings comprise a first bearing member (11) fixed in said loom frame (10) and a journal stud (12) secured to said support bracket (9) rotatably held in said first bearing member (11), and wherein said second bearings comprise a second bearing member (13) fixed in said support bracket (9) at each end of said faller roller and a bearing shaft (14) having ends journalled in said second bearing members (13) at opposite ends of said bearing shaft (14).

4. The apparatus of claim 1, comprising two control levers (48), one of which is rigidly secured to each end of said faller roller (8) and at least one biasing spring (46) connected to each control lever (48).

5. The apparatus of claim 1, wherein said support bracket (9) comprises an elongated hole (9C), wherein said one end (16A) of said coupling link (16) is adjustably connected to said support bracket (9) for adjusting a basic terry motion of said faller roller (8).

6. The apparatus of claim 5, further comprising a motorized position adjustment device connected to said one end (16A) of said coupling link (16) for controllably adjusting the position of said coupling link end (16A) along said elongated hole (9C).

7. The apparatus of claim 1, comprising two biasing springs, a tensioning device (51) on each side of said loom, each tensioning device comprising one of said two biasing springs, each tensioning device being connected to said other spring end of a respective biasing spring of said two biasing springs for varying the biasing spring force of said biasing springs (46), said tensioning device (51) comprising a guide slot (57) in each said support bracket (9), two slide members (60) one of which is slidably movable in each said guide slot (57), said other spring end being secured to said slide member (60), two threaded spindles (58) one on each loom side, each threaded spindle cooperating with one of said slide members (60), a female threading (58A) fixed in each of said slide members (60), each said threaded spindles (58) engaging a respective female threading (58A) for adjusting said biasing spring force by rotating said threaded spindles.

8. The apparatus of claim 7, further comprising a spindle drive motor (61) operatively connected to each of said threaded spindles (58).

9. The apparatus of claim 8, further comprising an electronic main loom control (MLC) operatively connected to said spindle drive motor for operating threaded spindles (58) in synchronism.

10. The apparatus of claim 1, further comprising a warp thread tension sensor (56) arranged between said guide roller (5) and said faller roller (8) for providing an actual warp tension representing signal to a main loom control (MLC).

11. The apparatus of claim 1, further comprising an electronic main loom control (MLC) operatively connected to said guide roller drive motor (5A) for influencing the warp tension.

12. The apparatus of claim 1, wherein said controllable drive (52) comprises a piston cylinder device pivoted to said loom frame (53) and to said control lever (48).

13. The apparatus of claim 11, wherein said guide roller drive motor (5A) is a d.c.-motor integrated into said drive roller (5).

14. The apparatus of claim 1, wherein said support bracket (9) comprises an angle lever including a first substantially vertically extending lever leg (9A) and a substantially horizontally extending lever leg (9B).

15. The apparatus of claim 1, wherein said controllable drive (52) comprises a piston cylinder device including a piston rod (52A) pivoted to said control lever (48), a fluid pressure source (69), pressurized fluid control valves (63, 64, 67, 68) and pressure fluid conduits or lines (65, 66) connecting said piston cylinder device (52) to said fluid pressure source through said fluid control valves, and an electronic main loom control (MLC) connected to said control valves for operating at least certain of said control valves in synchronism with a terry weaving motion of said terry weaving drive (17).

16. The apparatus of claim 15, wherein said fluid control valves comprise first valves (64, 68) connected to supply fluid under pressure to a first chamber in said piston cylinder device and second valves (63, 67) connected to a second chamber in said piston cylinder device.

17. The apparatus of claim 16, wherein said first chamber is positioned in a cylinder of said piston cylinder device opposite said piston rod, and wherein said second chamber is positioned so that said piston rod passes through said second chamber, and wherein said first chamber is pressurized through said first valves (64, 68) in synchronism with said terry drive (17) for producing terry cloth.

18. The apparatus of claim 16, wherein said first chamber is positioned in a cylinder of said piston cylinder device opposite said piston rod, and wherein said second chamber is positioned so that said piston rod passes through said second chamber, and wherein said second chamber is pressurized through said second valves (63, 67) in synchronism with said terry drive (17) for producing a smooth fabric.

* * * * *

UNITED STATES PATENT AND TRADEMARK OFFICE
CERTIFICATE OF CORRECTION

PATENT NO. : 5,722,464
DATED : Mar. 3, 1998
INVENTOR(S) : Truyen et al.

It is certified that error appears in the above-identified patent and that said Letters Patent is hereby corrected as shown below:

On the title page, under [75] Inventors:,
line 1, after "Oudenaarde" insert --, Belgium--;
line 2, after "Lindau-Bodolz" insert --, Germany--;
line 3, after "Wangen" insert --, Germany--;
line 4, after "Lindau" insert --, Germany--;
after "Hoerbranz" insert --, Austria--;
line 5, after "Lindau-Bodolz" delete ", all of" and instead insert --, Germany--;
line 6, delete "Germany";

Col. 2, line 26, after "and" delete "articularly" and instead insert --particularly--;
line 29, after "the" (first occurrence) delete "glide" and instead insert --guide--;

Col. 7, line 42, after "threaded" delete "female";
after "internal" insert --female--;

Col. 10, line 34, after "operating" insert --said--.

Signed and Sealed this

Twenty-sixth Day of May, 1998

Attest:

BRUCE LEHMAN

*Attesting Officer*   *Commissioner of Patents and Trademarks*